United States Patent
Lenich

(10) Patent No.: US 12,288,324 B2
(45) Date of Patent: Apr. 29, 2025

(54) PROVIDING A SCENE WITH SYNTHETIC CONTRAST

(71) Applicant: Siemens Healthcare GmbH, Erlangen (DE)

(72) Inventor: Tobias Lenich, Nuremberg (DE)

(73) Assignee: Siemens Healthineers AG, Forchheim (DE)

(*) Notice: Subject to any disclaimer, the term of this patent is extended or adjusted under 35 U.S.C. 154(b) by 535 days.

(21) Appl. No.: 17/392,397

(22) Filed: Aug. 3, 2021

(65) Prior Publication Data

US 2022/0051401 A1 Feb. 17, 2022

(30) Foreign Application Priority Data

Aug. 12, 2020 (DE) ...................... 10 2020 210 192.2

(51) Int. Cl.
*G06T 7/00* (2017.01)
*A61B 6/00* (2024.01)
(Continued)

(52) U.S. Cl.
CPC ............ *G06T 7/0012* (2013.01); *A61B 6/504* (2013.01); *A61B 6/5217* (2013.01); *G06T 7/579* (2017.01);
(Continued)

(58) Field of Classification Search
CPC ................... A61B 6/5217; G06T 5/50; G06T 2207/10016
See application file for complete search history.

(56) References Cited

U.S. PATENT DOCUMENTS 7,680,528 B2 * 3/2010 Pfister ...................... A61B 6/12
600/407
8,184,886 B2 5/2012 Khamene
(Continued)

FOREIGN PATENT DOCUMENTS

CN 111435542 A 7/2020
EP 3637362 A1 4/2020
WO WO-2016075331 A2 * 5/2016 ............. A61B 5/026

OTHER PUBLICATIONS

Ma et al. "Dynamic coronary roadmapping via catheter tip tracking in X-ray fluoroscopy with deep learning based Bayesian filtering," Medical Image Analysis, vol. 61, 2020, https://doi.org/10.1016/j.media.2020.101634 (Year: 2020).*
(Continued)

*Primary Examiner* — Ming Y Hon
*Assistant Examiner* — Julia Z. Yao
(74) *Attorney, Agent, or Firm* — Lempia Summerfield Katz LLC

(57) ABSTRACT

A computer-implemented method for providing a scene with synthetic contrast includes receiving preoperative image data of an examination region containing a hollow organ, wherein the medical image data images a contrast agent flow in the hollow organ; receiving intraoperative image data of the examination region of the examination subject, wherein the intraoperative image data images a medical object at least partially disposed in the hollow organ, generating the scene with synthetic contrast by applying a trained function to input data, wherein the input data is based on the preoperative image data and the intraoperative image data, wherein the scene with synthetic contrast images a virtual contrast agent flow in the hollow organ taking into account the medical object disposed therein, wherein at least one parameter of the trained function is based on a comparison
(Continued)

between a training scene and a comparison scene; and providing the scene with synthetic contrast.

10 Claims, 9 Drawing Sheets

(51) Int. Cl.
    *A61B 6/50*     (2024.01)
    *G06N 3/08*     (2023.01)
    *G06T 7/579*     (2017.01)
    *G16H 30/40*     (2018.01)

(52) U.S. Cl.
    CPC ............ *G16H 30/40* (2018.01); *G06N 3/08* (2013.01); *G06T 2207/10116* (2013.01); *G06T 2207/20081* (2013.01); *G06T 2207/30104* (2013.01)

(56) References Cited

U.S. PATENT DOCUMENTS

| | | | | |
|---|---|---|---|---|
| 9,292,917 | B2* | 3/2016 | Grbic | G06T 7/344 |
| 9,449,145 | B2* | 9/2016 | Sankaran | A61B 6/481 |
| 9,886,760 | B2 | 2/2018 | Liu | |
| 10,580,172 | B2* | 3/2020 | Qiu | G06T 5/50 |
| 10,818,073 | B2* | 10/2020 | Mistretta | A61B 6/463 |
| 2012/0059249 | A1 | 3/2012 | Verard et al. | |
| 2013/0294667 | A1* | 11/2013 | Zheng | G06T 7/30 |
| | | | | 382/131 |
| 2015/0178467 | A1* | 6/2015 | Britzen | G06T 19/00 |
| | | | | 703/11 |
| 2016/0148372 | A1* | 5/2016 | Itu | A61B 6/507 |
| | | | | 382/128 |
| 2018/0071452 | A1* | 3/2018 | Sharma | A61M 5/007 |
| 2018/0085078 | A1* | 3/2018 | Sankaran | G16H 10/60 |
| 2019/0038249 | A1* | 2/2019 | Itu | G06F 18/2413 |
| 2019/0247004 | A1* | 8/2019 | Taylor | A61B 8/481 |
| 2019/0251713 | A1* | 8/2019 | Chen | A61B 6/482 |
| 2020/0051258 | A1* | 2/2020 | Miao | G06V 20/653 |
| 2020/0117957 | A1 | 4/2020 | Birkhold et al. | |
| 2020/0226801 | A1 | 7/2020 | Kaethner et al. | |
| 2020/0273569 | A1 | 8/2020 | Sharma et al. | |
| 2020/0337773 | A1* | 10/2020 | Rawlinson | G06T 7/13 |
| 2021/0137634 | A1* | 5/2021 | Lang | A61B 5/113 |
| 2021/0248762 | A1 | 8/2021 | Pfister et al. | |
| 2023/0050982 | A1* | 2/2023 | Del Alamo de Pedro | A61B 8/485 |

OTHER PUBLICATIONS

Guan et al., "Deformable Cardiovascular Image Registration via Multi-Channel Convolutional Neural Network," in IEEE Access, vol. 7, pp. 17524-17534, 2019, doi: 10.1109/Access.2019.2894943. (Year: 2019).*

Kimura et al. Virtual digital subtraction angiography using multizone patch-based U-Net. Phys Eng Sci Med 43, 1305-1315 (2020). https://doi.org/10.1007/s13246-020-00933-9 (Year: 2020).*

German Office Action for German Application No. 10 2020 210 192.2 dated May 19, 2021.

* cited by examiner

PROVIDING A SCENE WITH SYNTHETIC CONTRAST

The present patent document claims the benefit of German Patent Application No. 10 2020 210 192.2, filed Aug. 12, 2020, which is hereby incorporated by reference in its entirety.

TECHNICAL FIELD

The disclosure relates to a computer-implemented method for providing a scene with synthetic contrast, a computer-implemented method for providing a trained function, a provisioning unit, a medical imaging device, a training unit, and a computer program product.

BACKGROUND

X-ray-based imaging methods are frequently employed in order to record changes over time in an examination region of an examination subject, for example, a human and/or animal patient. The change over time that is to be recorded may include a propagation motion and/or flow motion of a contrast agent, (e.g., of a contrast agent flow and/or a contrast agent bolus), in a hollow organ of the examination subject, in a vessel section of the latter, for example.

In this regard, the x-ray-based imaging methods may include a digital subtraction angiography (DSA) procedure, in which at least two x-ray images acquired in chronological sequence, which image at least part of the common examination region, are subtracted from one another. In a DSA, a distinction may also be made by subdividing the procedure into a mask phase for acquiring at least one mask image and a fill phase for acquiring at least one fill image. In this case, the mask image may image the examination region without contrast agent. Furthermore, the fill image may image the examination region while the contrast agent is disposed therein. A difference image may be provided as the result of the DSA by subtraction of mask and fill image. By this means, it may be possible to reduce and/or remove the components in the difference image that are irrelevant to and/or interfere with a treatment and/or diagnosis and in particular do not change over time.

In order to image a temporal dynamic of the contrast agent flow, (e.g., a propagation direction), in the examination region, multiple fill images may be acquired sequentially in time and combined with the mask image to produce a time-resolved difference image. A preoperative DSA is frequently performed as a preliminary act for planning a treatment of vascular malformations and/or vascular occlusions and/or stenoses. Because such a temporal dynamic of the contrast agent flow may be changed by introducing a medical object, (e.g., a catheter and/or an endoscope), into the hollow organ, a further DSA may be performed intraoperatively in order to monitor the treatment. In particular, the introduced medical object may lead to a deformation of the hollow organ and/or surrounding tissue, potentially resulting in an additional change in the temporal dynamic of the contrast agent flow. A disadvantageous aspect is that the current DSA methods are able to image such a change in the temporal dynamic only by a new acquisition of x-ray images with administration of contrast agent. This causes the examination subject to be additionally exposed to an increased x-ray and/or contrast agent dose.

SUMMARY AND DESCRIPTION

The object underlying the disclosure is therefore to intraoperatively provide a changed temporal dynamic of a contrast agent flow in a hollow organ caused by a medical object.

The scope of the present disclosure is defined solely by the appended claims and is not affected to any degree by the statements within this summary. The present embodiments may obviate one or more of the drawbacks or limitations in the related art.

The achievement of the object is described in the following disclosure both in relation to methods and devices for providing a scene with synthetic contrast and in relation to methods and devices for providing a trained function. In the process, features, advantages, and alternative embodiments of data structures and/or functions in methods and devices for providing a scene with synthetic contrast may be applied to analogous data structures and/or functions in methods and devices for providing a trained function. Analogous data structures in this context may be characterized in particular by the use of the prefix "training". Furthermore, the trained functions used in methods and devices for providing a scene with synthetic contrast may have been adapted and/or provided in particular by methods and devices for providing a trained function.

The disclosure relates in a first aspect to a computer-implemented method for providing a scene with synthetic contrast. This entails, in act b.1), receiving preoperative image data of an examination region of an examination subject. The examination region in this case contains a hollow organ. Furthermore, the medical image data images a contrast agent flow in the hollow organ. In act b.2), intraoperative image data of the examination region of the examination subject is received. In this case, the intraoperative image data images a medical object at least partially disposed in the hollow organ. In act b.3), the scene with synthetic contrast is generated by applying a trained function to input data, the input data being based on the preoperative image data and the intraoperative image data. Also, the scene with synthetic contrast images a virtual contrast agent flow in the hollow organ taking into account the medical object at least partially disposed therein. In this case, the scene with synthetic contrast advantageously signifies a time-resolved imaging of the virtual contrast agent flow in the hollow organ, the virtual contrast agent flow exhibiting a predefined contrast, in particular contrast value and/or intensity curve, in respect of anatomical structures and/or tissue of the examination subject. In particular, the predefined contrast of the virtual contrast agent flow may be consistent with a contrast of a real contrast agent, in particular with the contrast agent flow. The fact that the scene with synthetic contrast images the virtual contrast agent flow intraoperatively in the hollow organ means that this scene may be referred to as being synthetically contrasted.

Furthermore, at least one parameter of the trained function is based on a comparison between a training scene and a comparison scene. The scene with synthetic contrast is provided in act b.4).

The receiving of the preoperative and/or intraoperative image data may include an acquisition thereof and/or a readout thereof from a computer-readable data memory and/or a receiving thereof from a data storage unit, for example, a database. The preoperative and/or intraoperative image data may also be provided by a provisioning unit of a medical imaging device.

The examination subject may be a human and/or animal patient, for example. Furthermore, the examination region of the examination subject may include a spatial section, in particular a volume, of the examination subject which contains a hollow organ. The hollow organ may include a lung and/or a vessel section, for example, an artery and/or a vein and/or a heart.

The preoperative image data may advantageously image the examination region, in particular the hollow organ, preoperatively, e.g., at an earlier point in time than the intraoperative image data. In this case, the preoperative image data may include a two-dimensional (2D) and/or three-dimensional (3D) image of the examination region. Furthermore, the preoperative image data may image the examination region in a time-resolved manner. This advantageously enables the preoperative image data to provide a time-resolved image of the contrast agent flow in the hollow organ. The contrast agent flow may include a flow motion and/or propagation motion of a contrast agent in the hollow organ. Furthermore, the preoperative image data may contain multiple image elements, in particular pixels and/or voxels, where the image elements may have a time intensity curve in each case. The contrast agent flow may be imaged and/or acquired by an overshooting and/or undershooting of a predefined intensity threshold value in the time intensity curves. Furthermore, the preoperative image data may include metadata, in which case the metadata may include information about an acquisition parameter and/or operating parameter of the medical imaging device and/or information about the contrast agent flow at the time of the acquisition of the preoperative image data.

The intraoperative image data may advantageously image the examination region, in particular the hollow organ, intraoperatively, (e.g., at a later time than the preoperative image data). In this case, the intraoperative image data may include a 2D and/or 3D image of the examination region. Furthermore, the intraoperative image data may advantageously image a medical object at least partially disposed in the hollow organ. The medical object may include a surgical and/or diagnostic instrument, for example, a guide wire and/or a catheter and/or a laparoscope and/or an endoscope.

The medical imaging device for acquiring the intraoperative image data may be the same as or different from the medical imaging device for acquiring the preoperative image data.

The preoperative and/or the intraoperative image data may include at least one projection image, in particular an x-ray projection image, and/or a slice image of the examination region. In this case, the preoperative image data may image the examination region in accordance with a digital subtraction angiography (DSA), where the preoperative image data may contain at least one mask image, at least one fill image and/or at least one difference image. Furthermore, the preoperative and/or intraoperative image data may image the examination region along at least one spatial direction, in particular multiple and/or different spatial directions, in particular projection directions and/or angulations. Moreover, the preoperative image data may contain a time-resolved 3D image of the examination region, for example in accordance with a 4D-DSA, in particular a time-resolved 3D-DSA.

In act b.3), the scene with synthetic contrast may advantageously be generated by applying the trained function to the input data. The scene with synthetic contrast may contain an, in particular intraoperative, time-resolved 2D and/or 3D image of the examination region. The scene with synthetic contrast may include a sequence of individual images, the virtual contrast agent flow being imaged in the scene with synthetic contrast, in particular in the individual images. In this case, the scene with synthetic contrast may at least partially correspond to the intraoperative image data, in particular with regard to the imaging of the examination region. In particular, a spatial and/or temporal progression of the hollow organ and/or of the medical object may match in the respective imaging of the intraoperative image data and the scene with synthetic contrast. Furthermore, the scene with synthetic contrast may image the virtual contrast agent flow in the hollow organ taking into account the medical object disposed therein. The medical object disposed intraoperatively in the hollow organ may lead to a change in a flow dynamic within the hollow organ. Advantageously, the scene with synthetic contrast may image the hollow organ, in particular intraoperatively, the virtual contrast agent flow being imaged in the scene with synthetic contrast in a time-resolved manner taking into account the change in flow dynamic due to the medical object disposed in the hollow organ. For this purpose, the scene with synthetic contrast may advantageously contain multiple image elements, in particular pixels and/or voxels, where the image elements may have a time intensity curve in each case. The virtual contrast agent flow may be imaged by a change, in particular an overshooting and/or undershooting of a predefined intensity threshold value, in the time intensity curves.

The trained function may advantageously be trained by a machine learning method. In particular, the trained function may be a neural network, in particular a convolutional neural network (CNN) or a network including a convolutional layer.

The trained function maps input data to output data. In this case, the output data may furthermore be dependent on one or more parameters of the trained function. The one or more parameters of the trained function may be determined and/or adjusted by a training process. The determination and/or adjustment of the one or more parameters of the trained function may be based on a pairing composed of training input data and associated training output data, the trained function being applied to the training input data in order to generate training imaging data. The determination and/or adjustment may be based on a comparison of the training imaging data and the training output data. A trainable function, (e.g., a function having one or more parameters that have not yet been adjusted), may also be referred to as a trained function.

Other terms for trained function are trained mapping rule, mapping rule with trained parameters, function with trained parameters, artificial-intelligence-based algorithm, and machine learning algorithm. One example of a trained function is an artificial neural network, the edge weights of the artificial neural network corresponding to the parameters of the trained function. The term "neural net" may also be used instead of the term "neural network". In particular, a trained function may also be a deep neural network or deep artificial neural network. A further example of a trained function is a "support vector machine", while other machine learning algorithms may also be used as trained functions.

The trained function may be trained by a backpropagation. First, training imaging data may be determined by applying the trained function to training input data. Next, a deviation between the training imaging data and the training output data may be ascertained by applying an error function to the training imaging data and the training output data.

Furthermore, at least one parameter, (e.g., a weighting), of the trained function, (e.g., of the neural network), may be iteratively adjusted in respect of the at least one parameter of the trained function based on a gradient of the error function. By this means, the deviation between the training imaging data and the training output data may advantageously be minimized during the training of the trained function.

The trained function, in particular the neural network, advantageously has an input layer and an output layer. The input layer may be embodied for receiving input data. The output layer may furthermore be embodied for providing imaging data. The input layer and/or the output layer may each include a plurality of channels, in particular neurons.

At least one parameter of the trained function may be based on a comparison between a training scene and a comparison scene. In this case, the training scene and/or the comparison scene may advantageously be determined as part of a proposed computer-implemented method for providing a trained function, as will be explained in the further course of the description. In particular, the trained function may be provided by an embodiment of the proposed computer-implemented method for providing a trained function.

The providing of the scene with synthetic contrast in act b.4) may furthermore include a storing of the same on a computer-readable storage medium and/or a displaying of the same on a visualization unit and/or a transferring of the same to a provisioning unit. In particular, a graphical representation of the scene with synthetic contrast may be displayed on the visualization unit.

The proposed method enables a change in the temporal dynamic, in particular the flow dynamic, of a virtual contrast agent flow in a hollow organ having a medical object disposed therein to be provided intraoperatively. At the same time, an intraoperative administration of contrast agent may advantageously be dispensed with. Furthermore, a user, (e.g., a member of the medical staff), may be supported when planning a repositioning, (e.g., a changed arrangement), and/or when specifying an operating parameter of the medical object.

In a further advantageous embodiment of the proposed method for providing a scene with synthetic contrast, the scene with synthetic contrast may include a time-resolved 3D image of the virtual contrast agent flow taking into account the medical object at least partially disposed in the hollow organ.

Advantageously, the preoperative image data may provide a time-resolved 2D image of the examination region from at least two different spatial directions, in particular projection directions and/or angulations. Analogously thereto, the intraoperative image data may provide a 2D image of the examination region from at least two different spatial directions, in particular projection directions and/or angulations. Alternatively, or in addition, the preoperative and/or intraoperative image data may contain a time-resolved 3D image of the examination region. This enables the scene with synthetic contrast including the time-resolved 3D image of the virtual contrast agent flow in the hollow organ to be generated by the application of the trained function to the input data. Thus, the scene with synthetic contrast may advantageously provide a time-resolved three-dimensional image of a volume section of the examination region. This enables a three-dimensional curvature of the hollow organ and/or of the medical object to be detectable. Furthermore, it will be possible to detect, (e.g., distinguish), the virtual contrast agent flow in mutually overlaying and/or branching vessel sections of the hollow organ. The time-resolved 3D image of the virtual contrast agent flow may correspond to a 4D-DSA image and/or exhibit the features thereof.

Insofar as the intraoperative image data provides a time-resolved three-dimensional image of the examination region, the scene with synthetic contrast including the time-resolved 3D image of the virtual contrast agent flow may be overlaid and/or averaged, in particular weighted, with the intraoperative image data. This advantageously enables the virtual contrast agent flow to be integrated into the intraoperative image data, for example in a common graphical representation.

In a further advantageous embodiment of the proposed method for providing a scene with synthetic contrast, the scene with synthetic contrast may include at least one synthetic time-resolved 2D image of the virtual contrast agent flow taking into account the medical object at least partially disposed in the hollow organ.

In this case, the scene with synthetic contrast may provide a time-resolved 2D image of the virtual contrast agent flow in the hollow organ along a projection direction of the preoperative and/or intraoperative image data. Insofar as the intraoperative image data provides a 2D image of the examination region, the scene with synthetic contrast including the time-resolved 2D image of the virtual contrast agent flow may be overlaid and/or averaged, in particular weighted, with the intraoperative image data. This advantageously enables the virtual contrast agent flow to be integrated into the intraoperative image data, for example, in a common graphical representation. If the acquisition geometry for acquiring the intraoperative image data is changed, the generation of the image data with synthetic contrast may advantageously be performed repeatedly by the application of the trained function to the input data. By this, it may be provided that the projection direction of the scene with synthetic contrast is additionally consistent with the projection direction for imaging the intraoperative image data.

In a further advantageous embodiment of the proposed method for providing a scene with synthetic contrast, the at least one synthetic time-resolved 2D image may be generated by a virtual projection of the time-resolved 3D image.

The generation of the time-resolved 2D image may advantageously include a virtual projection of the 3D image along a projection direction of the preoperative and/or intraoperative image data onto a virtual detector. In particular, an imaging geometry of the virtual projection may coincide with an acquisition geometry for acquiring the preoperative and/or intraoperative image data. By generating the time-resolved 2D image by the virtual projection of the 3D image, it is possible to adjust the projection direction in a particularly computationally efficient manner, for example, to a changed projection direction for acquiring the intraoperative image data. Furthermore, a user may adjust the projection direction and/or the imaging geometry for generating the time-resolved 2D image, in particular dynamically, by an input by an input unit. This enables a particularly intuitive generation and/or graphical representation of the synthetic scene, in particular of the time-resolved 2D image.

In a further advantageous embodiment of the proposed method for providing a scene with synthetic contrast, the input data may additionally be based on a material parameter and/or an operating parameter and/or shape information relating to the medical object and/or on a physiological parameter of the examination subject.

The material parameter may include material information relating to the medical object, in particular, with regard to a porosity and/or stiffness and/or flexibility and/or compressibility thereof. Furthermore, the operating parameter may include information with regard to an, in particular current, positioning, in particular position and/or orientation, of the medical object. The shape information may also include information in respect of a diameter and/or circumference and/or cross-section and/or surface, in particular a volume model and/or volume mesh model, and/or a curvature and/or a spatial progression of the medical object. Furthermore, the shape information may advantageously include information with regard to a surface texture of the medical object, in particular information in respect of indentations and/or elevations on the surface of the medical object. Advantageously, the material parameter and/or the operating parameter and/or the shape information may describe a condition of the medical object at the time of the acquisition of the intraoperative image data.

Furthermore, the physiological parameter may include a breath signal and/or a motion signal and/or a pulse signal and/or blood pressure information relating to the examination subject, in particular at the time of the acquisition of the preoperative and/or intraoperative image data. Insofar as the physiological parameter reflects a condition of the examination subject during the acquisition of the preoperative image data, the contrast agent flow imaged in the preoperative image data may be characterized particularly precisely.

In particular, the material parameter and/or the operating parameter and/or the shape information relating to the medical object and/or the physiological parameter of the examination subject may be received in act b.1) and/or b.2). The receiving of the material parameter and/or of the operating parameter and/or of the shape information relating to the medical object and/or of the physiological parameter of the examination subject may include an acquisition thereof and/or a readout thereof from a computer-readable data memory and/or a receiving thereof from a data storage unit, for example, a database. Furthermore, the material parameter and/or the operating parameter and/or the shape information may be provided by the medical object, in particular by a processing unit of the medical object. Furthermore, the physiological parameter of the examination subject may be provided by a sensor for detecting the physiological parameter, for example, a breath sensor and/or a motion sensor and/or a pulse sensor and/or a blood pressure sensor.

By adding the material parameter and/or the operating parameter and/or the shape information relating to the medical object and/or the physiological parameter of the examination subject, the scene with synthetic contrast, (e.g., the virtual contrast agent flow), may advantageously be adjusted with a high degree of accuracy and particularly effectively to an, in particular current, condition of the medical object and/or of the examination subject.

In a further advantageous embodiment of the proposed method for providing a scene with synthetic contrast, the input data may additionally be based on a contrast agent flow parameter and/or a virtual contrast agent flow parameter. In this case, the parameter may specify a dose and/or motion speed and/or motion direction of the virtual contrast agent flow.

The contrast agent flow parameter may be provided, for example, by a device for monitoring a contrast agent injection at the time of the acquisition of the preoperative image data. Alternatively, the contrast agent flow parameter may be determined from the preoperative image data, for example, by a bolus tracking method and/or an analysis of the time intensity curves of the preoperative image data. The contrast agent flow parameter may include information in respect of a dose and/or an injection rate and/or a flow velocity and/or a viscosity and/or an injection site of the contrast agent flow at the time of the acquisition of the preoperative image data.

The virtual contrast agent flow parameter may advantageously be enterable and/or adjustable, (e.g., dynamically adjustable), by an input by a user, (e.g., by an input unit). Furthermore, the scene with synthetic contrast, in particular the virtual contrast agent flow, may be generated for a predefined value range of the virtual contrast agent flow parameter, where the value range may include a plurality of different values for the virtual contrast agent flow parameter. The virtual contrast agent flow parameter may specify a dose and/or a virtual injection rate of the virtual contrast agent flow. Furthermore, the virtual contrast agent flow parameter may specify a motion speed, in particular a flow velocity and/or propagation rate and/or viscosity, of the virtual contrast agent flow, in particular of a virtual contrast agent bolus. The virtual contrast agent flow may be generated in such a way that at least one virtual contrast agent bolus, in particular multiple successive virtual contrast agent boli, is/are imaged in the scene with synthetic contrast.

Advantageously, the virtual contrast agent flow in the scene with synthetic contrast may be adjustable, in particular dynamically, by the specification of the virtual contrast agent flow parameter by the user. In particular, a graphical representation of the synthetic scene may be displayed by the visualization unit, in which case the user may input and/or adjust the virtual contrast agent flow parameter by the input unit.

The disclosure relates in a second aspect to a computer-implemented method for providing a trained function. In this case, in act t.1), preoperative training image data of a training examination region of a training examination subject is received. The training examination region also contains a hollow organ. Furthermore, the preoperative training image data images a contrast agent flow in the hollow organ. In act t.2), intraoperative training image data of the training examination region of the training examination subject is received. In this case, the intraoperative training image data images a medical object at least partially disposed in the hollow organ. In act t.3), a contrast-weighted comparison scene of a medical imaging device is received. In this case, the contrast-weighted comparison scene images a further contrast agent flow in the hollow organ, the medical object being at least partially disposed in the hollow organ. Alternatively, or in addition, a comparison scene with synthetic contrast is generated in act t.3) by applying a deformation correction to the preoperative training image data. In this case, the deformation correction is based on the intraoperative training image data. Furthermore, the comparison scene with synthetic contrast images a virtual comparison contrast agent flow in the hollow organ taking into account the medical object at least partially disposed therein, the virtual comparison contrast agent flow being simulated.

In act t.4), a training scene with synthetic contrast is generated by applying the trained function to input data, which input data is based on the preoperative and the intraoperative training image data. In act t.5), at least one parameter of the trained function is adjusted based on a comparison between the training scene and the comparison scene. The trained function is provided in act t.6).

The receiving of the preoperative and/or intraoperative training image data and/or the comparison scene with contrast may include an acquisition thereof and/or a readout thereof from a computer-readable data memory and/or a receiving thereof from a data storage unit, for example, a database. Furthermore, the preoperative and/or intraoperative training image data and/or the comparison scene with contrast may be provided by a provisioning unit of a further medical imaging device. In this case, the further medical imaging device may be the same as or different from the medical imaging device for acquiring the preoperative and/or intraoperative image data. The further medical imaging device for acquiring the intraoperative training image data may also be the same as or different from the further medical imaging device for acquiring the preoperative training image data sein.

The preoperative training image data may possess all properties of the preoperative image data that have been described in relation to the computer-implemented method for providing a scene with synthetic contrast, and vice versa. Furthermore, the intraoperative training image data may possess all properties of the intraoperative image data that have been described in relation to the computer-implemented method for providing a scene with synthetic contrast, and vice versa. The preoperative and/or intraoperative training image data may also be simulated.

The preoperative training image data may advantageously image the training examination region, in particular the hollow organ, preoperatively, (e.g., at an earlier time than the intraoperative training image data). The training examination region may possess all properties that have been described in relation to the computer-implemented method for providing a scene with synthetic contrast, and vice versa. Advantageously, the training examination region, (e.g., the hollow organ), may at least partially include an anatomical region substantially similar to the examination region. The training examination subject may be a human and/or animal patient and/or a vessel phantom. Furthermore, the training examination subject may advantageously be different from the examination subject. For example, the preoperative and/or intraoperative training image data and/or the comparison scene with contrast may be received for a plurality of different training examination subjects and/or training examination regions. The medical object described in relation to the computer-implemented method for providing a trained function may advantageously match at least to some extent that described in relation to the computer-implemented method for providing a scene with synthetic contrast, in particular with regard to a type and/or material and/or a material parameter and/or a shape and/or an operating parameter.

The comparison scene with contrast may advantageously have been acquired by the same or a different medical imaging device as the preoperative and/or intraoperative training image data. In this case, the comparison scene with contrast may contain an, (e.g., intraoperative), time-resolved 2D and/or 3D image of the training examination region, (e.g., of the hollow organ), the further contrast agent flow and the medical object being at least partially disposed in the training examination region, in particular in the hollow organ. The comparison scene with contrast may be embodied in particular as a sequence of individual images, the further contrast agent flow being imaged in the comparison scene with contrast, in particular in the individual images. In this case, the comparison scene with contrast may correspond at least partially to the intraoperative training image data, in particular with regard to the imaging of the examination region. The medical object intraoperatively disposed in the hollow organ may lead to a change in a flow dynamic within the hollow organ. Advantageously, the comparison scene with contrast may image the hollow organ, in particular intraoperatively, the further contrast agent flow and the medical object disposed in the hollow organ being imaged in a time-resolved manner in the comparison scene with contrast. For this purpose, the comparison scene with contrast may advantageously contain multiple image elements, (e.g., pixels and/or voxels), where the image elements may have a comparison time intensity curve in each case. The further contrast agent flow may be imaged for example by a change, in particular an overshooting and/or undershooting of a predefined intensity threshold value, in the comparison time intensity curves.

Alternatively, or in addition, a comparison scene with synthetic contrast may be generated by applying a deformation correction to the preoperative training image data. The deformation correction may be based on a progression of the medical object in the intraoperative training image data. In particular, the progression of the medical object in the hollow organ may be determined in the intraoperative image data by a segmentation of the medical object and/or an identification, in particular localization, of a marker structure disposed on the medical object. Immediately thereafter, a deformation correction algorithm may be applied to the preoperative training image data that images the contrast agent flow in the hollow organ based on the intraoperative progression of the medical object in the hollow organ. This enables the preoperative training image data, in particular the hollow organ imaged therein, to be adjusted to a spatial progression of the hollow organ in the intraoperative training image data. It may furthermore be achieved by this means that the contrast agent flow imaged in a time-resolved manner in the preoperative training image data follows the intraoperative progression of the hollow organ and/or of the medical object in the intraoperative training image data. However, it should be noted here that after the deformation correction has been applied to the preoperative training image data, the progression of the preoperative contrast agent is additionally imaged in the deformation-corrected preoperative training image data without taking into account the medical object intraoperatively disposed in the hollow organ.

The simulation of the virtual comparison contrast agent flow may advantageously be based on a numerical flow mechanics technique known as computational fluid dynamics (CFD), where a change in flow dynamic caused by the medical object intraoperatively disposed in the hollow organ may be taken into account for the virtual contrast agent flow. For this purpose, the simulation may include a virtual representation, (e.g., a 3D model), of the medical object, where the virtual representation of the medical object may be generated on the basis of the intraoperative image data, (e.g., by segmentation of the medical object and/or identification, in particular localization, of the marker structure disposed thereon). The simulation may advantageously be based on the deformation-corrected preoperative training image data and the intraoperative training image data; in particular, the simulation may be based on a spatial progression of the deformation-corrected hollow organ and/or a spatial progression of the intraoperatively imaged medical object.

In act t.4), the training scene with synthetic contrast may be generated by applying the trained function to input data. In this case, the input data may be based on the preoperative and the intraoperative training image data. In act t.5), the at least one parameter of the trained function may furthermore be adjusted based on a comparison between the training scene and the comparison scene. The comparison between the training scene and the comparison scene may advantageously be conducted image element by image element. In particular, the comparison may include determining a deviation between training time intensity curves of image elements of the training scene and the comparison intensity curves of the image elements of the comparison scene. In this case, the at least one parameter of the trained function may advantageously be adjusted in such a way that a deviation between the training scene and the comparison scene, in particular the deviation between the training time intensity curves of the image elements of the training scene and the comparison intensity curves of the image elements of the comparison scene, is minimized.

This advantageously enables a precision in the generation of the scene with synthetic contrast to be improved by the application of the trained function to the input data.

The providing of the trained function may include a storing of the same on a computer-readable storage medium and/or a transfer of the same to a provisioning unit.

A trained function suitable for use in an embodiment of the computer-implemented method for providing a scene with synthetic contrast may advantageously be provided by the proposed method.

In a further advantageous embodiment of the proposed method for providing a trained function, the comparison scene may include a time-resolved 3D comparison image of the further contrast agent flow and/or of the virtual comparison contrast agent flow taking into account the medical object at least partially disposed in the hollow organ.

The comparison scene may advantageously contain at least one time-resolved 3D comparison image that images the training examination region. In particular, the time-resolved 3D comparison image may image a volume section of the training examination region in a time-resolved 3D manner. This enables an intraoperative imaging of a 3D curvature of the hollow organ and/or of the medical object at least partially disposed in the hollow organ. Furthermore, the further contrast agent flow and/or the virtual comparison contrast agent flow may be detectable, in particular distinguishable, in mutually overlaying and/or branching vessel sections of the hollow organ by the 3D comparison image. The time-resolved 3D comparison image of the further contrast agent flow and/or of the virtual comparison contrast agent flow may include a 4D-DSA image, in particular a time-resolved 3D-DSA, and/or its features. The time-resolved 3D comparison image may furthermore contain multiple image elements, where the image elements may have a comparison time intensity curve in each case. The further contrast agent flow and/or the virtual comparison contrast agent flow may be imaged and/or detected based on an overshooting and/or undershooting of a predefined intensity threshold value in the comparison time intensity curves.

It may advantageously be achieved by this means that the trained function generates the training scene with synthetic contrast containing at least one time-resolved 3D training image. In this case, the comparison between the training scene and the comparison scene may advantageously include a comparison between the time-resolved 3D training image and the time-resolved 3D comparison image. The comparison between the time-resolved 3D training image and the time-resolved 3D-comparison image may be conducted image element by image element, in particular between training time intensity curves of the 3D training image and comparison time intensity curves of the 3D comparison image of mutually corresponding image elements in each case.

In a further advantageous embodiment of the proposed method for providing a trained function, the comparison scene may include at least one time-resolved 2D comparison image of the further contrast agent flow and/or of the virtual comparison contrast agent flow taking into account the medical object at least partially disposed in the hollow organ.

Advantageously, the comparison scene may contain at least one time-resolved 2D comparison image which images the training examination region along at least one spatial direction. For example, the 2D comparison image may contain a projection image, (e.g., an x-ray projection image), of the examination subject. Alternatively, or in addition, the 2D comparison image may contain a slice image of the training examination region. Furthermore, the comparison scene may contain multiple 2D comparison images that image the training examination region along different spatial directions in a time-resolved manner in each case, for example, projection images along multiple projection directions. The at least one time-resolved 2D comparison image may also contain multiple image elements, where the image elements may have a comparison time intensity curve in each case. The further contrast agent flow and/or the virtual comparison contrast agent flow may be imaged and/or detected based on an overshooting and/or undershooting of a predefined intensity threshold value in the comparison time intensity curves.

It may advantageously be achieved by this means that the trained function generates the training scene with synthetic contrast containing at least one time-resolved 2D training image. In this case, the comparison between the training scene and the comparison scene may advantageously include a comparison between the at least one time-resolved 2D training image and the at least one time-resolved 2D comparison image. The comparison between the at least one time-resolved 2D training image and the at least one time-resolved 2D comparison image may be conducted image element by image element, in particular between training time intensity curves of the 3D training image and comparison time intensity curves of the 3D comparison image of image elements corresponding to one another in each case.

In a further advantageous embodiment of the proposed method for providing a trained function, the at least one time-resolved 2D comparison image may be generated by a virtual projection of the time-resolved 3D comparison image.

The generation of the time-resolved 2D comparison image may advantageously include a virtual projection, (e.g., an intensity projection), of the 3D comparison image originating from a virtual x-ray source along a projection direction, (e.g., a projection direction of the preoperative and/or intraoperative training image data), onto a virtual detector. In particular, an imaging geometry of the virtual projection may correspond to an acquisition geometry for acquiring the preoperative and/or intraoperative training image data. By generating the time-resolved 2D comparison image by the virtual projection of the 3D comparison image, it is possible to adjust the projection direction in a particularly computationally efficient manner, for example, to a change in projection direction of the intraoperative training image data.

The embodiment described here may be advantageous when the synthetic training scene containing at least one 2D training image of the training examination region is generated by the application of the trained function, the comparison scene containing a 3D comparison image of the training examination region. The virtual projection of the 3D comparison image for generating the at least one 2D comparison image enables a comparison between the at least one 2D training image and the at least one 2D comparison image, where the at least one parameter of the trained function may be adjusted based on the comparison.

In a further advantageous embodiment of the proposed method for providing a trained function, the virtual comparison contrast agent flow may be simulated taking into account a deformation and/or constriction of a cross-section of the hollow organ caused by the medical object.

Advantageously, a progression and/or volume model of the hollow organ may be generated and/or adjusted on the basis of the preoperative training image data, for example, by segmentation of the hollow organ in the preoperative training image data. This is made possible in particular by the contrast agent flow disposed in the hollow organ at the time of the acquisition of the preoperative training image data. As a result of this, the preoperative training image data may include a contrast-weighted image of the hollow organ. The progression and/or volume model of the hollow organ may contain a, (e.g., deformable), 2D or 3D centerline model and/or volume mesh model. This progression and/or volume model may advantageously be adjusted, (e.g., deformation-corrected), by applying the deformation correction to the preoperative training image data in accordance with the progression of the medical object in the intraoperative training image data. Furthermore, the simulation of the virtual comparison contrast agent flow may be based on the deformation-corrected progression and/or volume model of the hollow organ. This advantageously enables the deformation of the hollow organ due to the medical object to be taken into account for the simulation of the virtual comparison contrast agent flow. Also, it may advantageously be achieved that the virtual contrast agent flow, which is imaged in the training scene with synthetic contrast, is likewise determined taking into account a deformation of the hollow organ due to the medical object at least partially disposed therein.

Furthermore, a constriction of a cross-section of the hollow organ due to the medical object intraoperatively disposed at least partially therein may be taken into account for the simulation of the virtual comparison contrast agent flow. For this purpose, the simulation of the virtual comparison contrast agent flow may be based on training shape information relating to the medical object, for example, on information in respect of a diameter and/or circumference and/or cross-section and/or a surface, in particular a volume model and/or volume mesh model, and/or a curvature and/or a spatial progression of the medical object. Furthermore, the training shape information may advantageously include information with regard to a surface texture of the medical object, in particular information in respect of indentations and/or elevations on the surface of the medical object. Furthermore, the simulation of the virtual comparison contrast agent flow may be based on a training material parameter and/or a training operating parameter of the medical object, in particular at the time of the acquisition of the intraoperative training image data. In this case, the training material parameter may describe a porosity and/or a material property of the medical object. Furthermore, the training operating parameter may include information relating to a positioning, in particular an orientation and/or spatial position, of the medical object.

Advantageously, the virtual comparison contrast agent flow may be precisely simulated taking into account the constriction of the cross-section of the hollow organ due to the medical object at least partially disposed therein. In this case, the simulation of the virtual comparison contrast agent flow, which is advantageously based on computational fluid dynamics, may be adjusted to the spatial progression of the hollow organ and/or of the medical object. By this, it may advantageously be achieved that the virtual contrast agent flow, which is imaged in the training scene with synthetic contrast, is likewise determined taking into account a constriction of the cross-section of the hollow organ due to the medical object at least partially disposed therein.

In a further advantageous embodiment of the proposed method for providing a trained function, the input data may additionally be based on a training material parameter and/or a training operating parameter and/or training shape information relating to the medical object and/or on a physiological training parameter of the training examination subject.

The training material parameter and/or training operating parameter and/or the training shape information relating to the medical object may contain all properties of the material parameter and/or operating parameter and/or of the shape information relating to the medical object that have been described hereinabove and/or in relation to the computer-implemented method for providing a scene with synthetic contrast, and vice versa. Furthermore, the physiological training parameter of the training examination subject may advantageously contain all properties of the physiological parameter of the examination subject that have been described in relation to the computer-implemented method for providing a scene with synthetic contrast, and vice versa.

In particular, the training material parameter and/or the training operating parameter and/or the training shape information relating to the medical object and/or the physiological training parameter of the training examination subject may be received in act t.1) and/or t.2) and/or t.3). The receiving of the training material parameter and/or of the training operating parameter and/or of the training shape information relating to the medical object and/or of the physiological training parameter of the training examination subject may include an acquisition thereof and/or a readout thereof from a computer-readable data memory and/or a receiving thereof from a data storage unit, for example, a database. Furthermore, the training material parameter and/or the training operating parameter and/or the training shape information may be provided by the medical object, in particular by a processing unit of the medical object. Moreover, the physiological training parameter of the training examination subject may be provided by a sensor for detecting the physiological training parameter, for example, a breath sensor and/or a motion sensor and/or a pulse sensor and/or a blood pressure sensor.

By adding the training material parameter and/or the training operating parameter and/or the training shape information relating to the medical object and/or the physiological training parameter of the training examination subject, it is advantageously possible to determine the training scene with synthetic contrast, (e.g., the virtual contrast agent flow), with a high degree of accuracy and particularly effectively adjusted to a condition of the medical object and/or of the training examination subject, in particular at the time of the acquisition of the intraoperative training image data.

In a further advantageous embodiment of the proposed method for providing a trained function, the input data may additionally be based on a training parameter for the further contrast agent flow and/or for the virtual comparison contrast agent flow. In this case, the training parameter may specify a dose and/or motion speed and/or motion direction of the virtual contrast agent flow.

The training parameter for the further contrast agent flow and/or for the virtual comparison contrast agent flow may contain all properties of the contrast agent flow parameter that have been described in relation to the computer-implemented method for providing a scene with synthetic contrast, and vice versa. Advantageously, the virtual contrast agent flow in the training scene may be generated based on the training parameter for the further contrast agent flow and/or for the virtual comparison contrast agent flow by applying the trained function to the input data. This may be advantageous when the further contrast agent flow and/or the virtual comparison contrast agent flow deviates in terms of a dose and/or motion speed and/or motion direction from the contrast agent flow at the time of the acquisition of the preoperative training image data. A particularly flexible, in particular dynamic, adjustment of the virtual contrast agent flow, (e.g., by an input of the user by the input unit), may be made possible by this means.

The disclosure relates in a third aspect to a provisioning unit which is embodied to perform the previously described computer-implemented methods for providing a scene with synthetic contrast and their aspects. The provisioning unit may advantageously include a computing unit, a memory unit, and an interface. The provisioning unit may be embodied to perform these methods and their aspects in that the interface and the computing unit are embodied to perform the corresponding method acts. In particular, the interface may be embodied to perform act b.1), b.2) and/or b.4). Furthermore, the computing unit and/or the memory unit may be embodied to perform act b.3).

The advantages of the proposed provisioning unit substantially correspond to the advantages of the proposed computer-implemented method for providing a scene with synthetic contrast. Features, advantages, or alternative embodiments mentioned in this context may equally be applied also to the other claimed subject matters, and vice versa.

The disclosure relates in a fourth aspect to a training unit which is embodied to perform the previously described computer-implemented methods for providing a trained function and their aspects. The training unit advantageously includes a training interface, a training memory unit, and a training computing unit. The training unit may be embodied to perform these methods and their aspects in that the training interface, the training memory unit and the training computing unit are embodied to perform the corresponding method acts. In particular, the training interface may be embodied to perform act t.1), t.2), t.3) and/or t.6). Furthermore, the training computing unit and/or the training memory unit may be embodied to perform act t.3) to t.5).

The advantages of the proposed training unit substantially correspond to the advantages of the proposed computer-implemented method for providing a trained function. Features, advantages, or alternative embodiments mentioned in this context may equally be applied also to the other claimed subject matters, and vice versa.

The disclosure relates in a fifth aspect to a medical imaging device, in particular including a proposed provisioning unit. In this case, the medical x-ray device, in particular the provisioning unit, is embodied to perform a proposed computer-implemented method for providing a scene with synthetic contrast. The medical imaging device is further embodied for acquiring and/or for receiving and/or for providing preoperative and/or intraoperative image data. The medical imaging device may be embodied as a medical x-ray device, in particular as a medical C-arm x-ray device, and/or as a computed tomography (CT) system and/or as a magnetic resonance (MRT) system and/or as an ultrasound system.

The advantages of the proposed medical x-ray device substantially correspond to the advantages of the proposed computer-implemented method for providing a scene with synthetic contrast. Features, advantages, or alternative embodiments mentioned in this context may equally be applied also to the other claimed subject matters, and vice versa.

The disclosure relates in a sixth aspect to a computer program product including a computer program which may be loaded directly into a memory of a provisioning unit, the computer program product having program sections for performing all acts of the computer-implemented method for providing a scene with synthetic contrast when the program sections are executed by the provisioning unit; and/or which may be loaded directly into a training memory of a training unit, having program sections for performing all acts of the proposed method for providing a trained function and/or one of its aspects when the program sections are executed by the training unit.

The disclosure relates in a seventh aspect to a computer-readable storage medium on which program sections that may be read and executed by a provisioning unit are stored for the purpose of performing all acts of the computer-implemented method for providing a scene with synthetic contrast when the program sections are executed by the provisioning unit; and/or on which program sections that may be read and executed by a training unit are stored for the purpose of performing all acts of the method for providing a trained function and/or one of its aspects when the program sections are executed by the training unit.

The disclosure relates in an eighth aspect to a computer program or computer-readable storage medium including a trained function provided by a proposed computer-implemented method or one of its aspects.

A largely software-based implementation has the advantage that provisioning units and/or training units already used previously in the prior art may also be easily upgraded by a software update in order to operate in the manner according to the disclosure. In addition to the computer program, such a computer program product may, where appropriate, include additional constituent parts such as a set of documentation and/or additional components, as well as hardware components, such as hardware keys (dongles, etc.) to enable use of the software.

BRIEF DESCRIPTION OF THE DRAWINGS

Exemplary embodiments of the disclosure are illustrated in the drawings and are described in more detail hereinbelow. The same reference characters are used for like features in different figures, in which.

DETAILED DESCRIPTION

Figure 1:
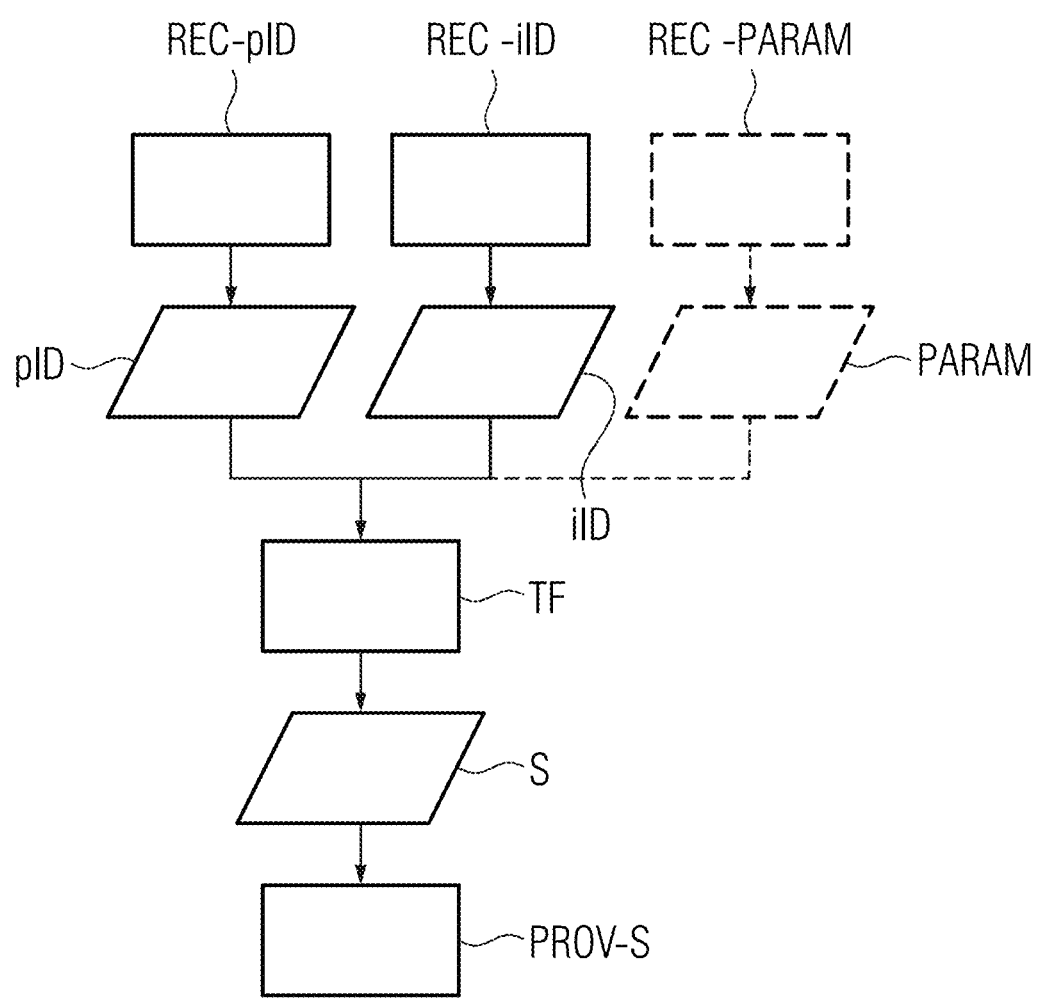
FIG. 1 depicts a schematic representation of an advantageous embodiment of the proposed method for providing a scene with synthetic contrast.

FIG. 1 depicts a schematic representation of an advantageous embodiment of the proposed method for providing a scene with synthetic contrast PROV-S. Herein, in act b.1), preoperative image data pID of an examination region of an examination subject may be received REC-pID. The examination region may contain a hollow organ, in which case the preoperative image data pID may image a contrast agent flow in the hollow organ. Intraoperative image data iID of the examination region of the examination subject may be received REC-iID in act b.2). In this case, the intraoperative image data iID may image a medical object at least partially disposed in the hollow organ. In act b.3), the scene with synthetic contrast S may be generated by applying a trained function TF to input data, where the input data of the trained function may be based on the preoperative image data pID and the intraoperative image data iID. Furthermore, the scene with synthetic contrast S may image a virtual contrast agent flow in the hollow organ taking into account the medical object disposed therein. Furthermore, at least one parameter of the trained function TF may be based on a comparison between a training scene and a comparison scene. The scene with synthetic contrast S may be provided PROV-S in act b.4).

Furthermore, the proposed method for providing a scene with contrast PROV-S may include a receiving REC-PARAM of a parameter PARAM, which parameter PARAM may include a material parameter and/or an operating parameter and/or shape information relating to the medical object MO and/or a physiological parameter of the examination subject. Advantageously, the input data of the trained function TF may be based in addition on the parameter PARAM. In this case, the parameter PARAM may be provided by the medical object MO, in particular by a processing unit of the medical object. Furthermore, the parameter PARAM, in particular the physiological parameter of the examination subject, may be provided by a sensor for detecting the physiological parameter, for example, a breath sensor and/or a motion sensor and/or a pulse sensor and/or a blood pressure sensor.

Furthermore, the parameter PARAM may include a parameter for the contrast agent flow pFI and/or a parameter for the virtual contrast agent flow vFI, which may specify a dose and/or motion speed and/or motion direction of the virtual contrast agent flow. The parameter for the virtual contrast agent flow vFI may be specified and/or adjusted by a user by an input unit. Furthermore, the parameter for the contrast agent flow pFI may be provided by a device for monitoring a contrast agent injection at the time of the acquisition of the preoperative image data pID.

Figure 2:
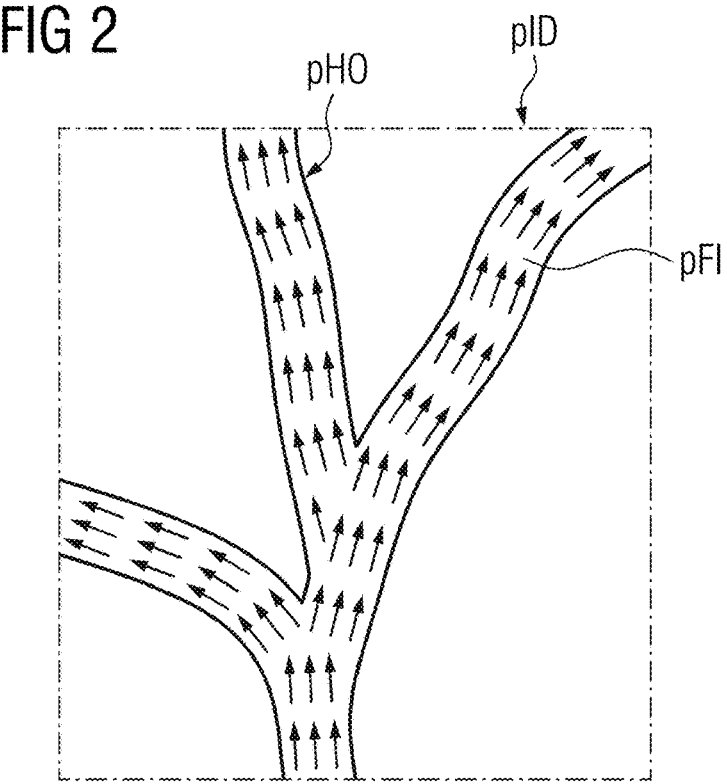
FIG. 2 depicts a schematic representation of an example of preoperative image data.
Figure 3:
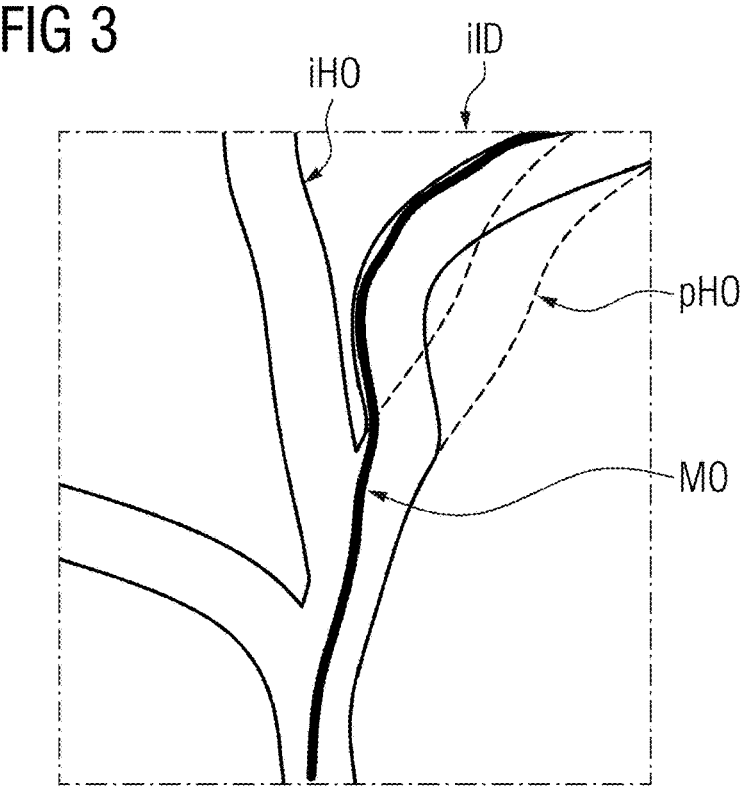
FIG. 3 depicts a schematic representation of an example of intraoperative image data.

Preoperative image data pID and intraoperative image data iID are represented schematically in FIG. 2 and FIG. 3, respectively. Here, the preoperative image data pID may image the contrast agent flow pFI (illustrated schematically by arrows in this case) preoperatively in the hollow organ pHO, a vessel section, for example. The preoperative image data pID may have been acquired by a DSA, for example.

The intraoperative image data iID illustrated schematically in FIG. 3 may advantageously image the medical object MO intraoperatively disposed at least partially in the hollow organ iHO. Compared to a preoperative progression of the hollow organ pHO, the medical object MO intraoperatively disposed at least partially in the hollow organ iHO may lead to a deformation of the hollow organ iHO.

Figure 4:
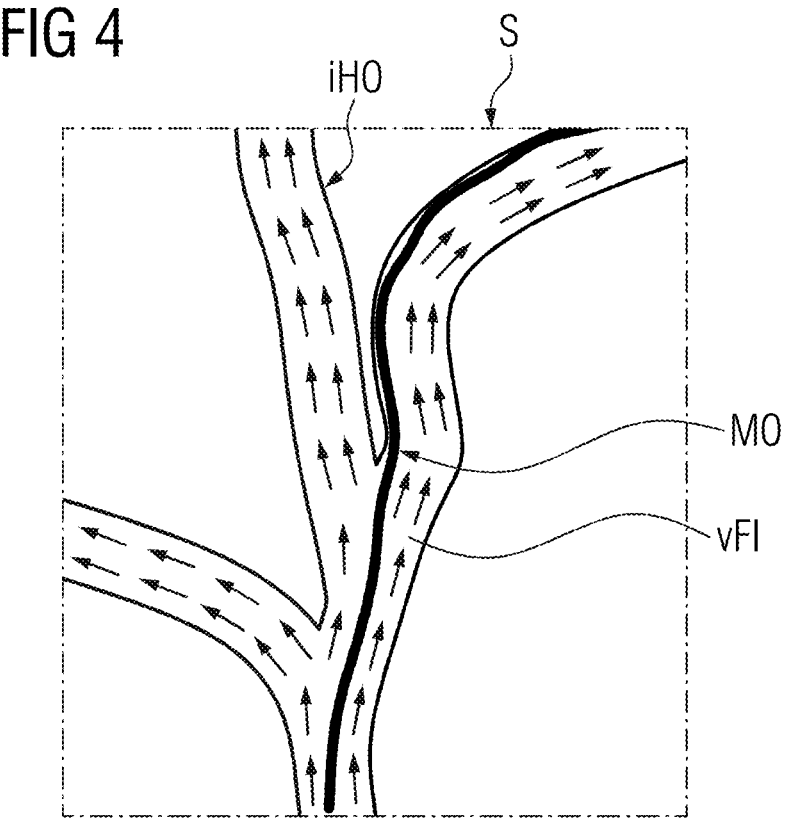
FIG. 4 depicts a schematic representation of an example of a scene with synthetic contrast.

A scene with synthetic contrast S, in particular an individual image of the scene with synthetic contrast S, is represented schematically in FIG. 4. The scene with synthetic contrast S may advantageously image the virtual contrast agent flow vFI intraoperatively in the hollow organ iHO taking into account the medical object MO at least partially disposed therein. In particular, the scene with synthetic contrast S may image the virtual contrast agent flow vFI taking into account the deformation and/or constriction of a cross-section of the hollow organ iHO due to the medical object (illustrated schematically by arrows in this case). The scene with synthetic contrast S may include a graphical representation of the virtual contrast agent flow vFI, (e.g., a color-coded and/or grayscale value-based and/or abstracted representation), which may be perceived visually by a user. Furthermore, the graphical representation of the virtual contrast agent flow vFI may in each case include a time intensity curve of at least one image element of the scene with synthetic contrast. Advantageously, the user, (e.g., a member of the medical staff), may be supported with the aid of the scene with synthetic contrast S, (e.g., the graphical representation of the virtual contrast agent flow vFI), when planning a repositioning, (e.g., a changed arrangement), of the medical object MO and/or when specifying an operating parameter of the medical object MO.

Furthermore, the scene with synthetic contrast S, (e.g., the graphical representation of the virtual contrast agent flow vFI), may include an image, (e.g., a color-coded image), of a deviation between the virtual contrast agent flow vFI and the contrast agent flow pFI. In particular, a deformation correction may be applied to the preoperative image data pID for this purpose, where the graphical representation may include a difference and/or a quotient between the deformation-corrected preoperative image data pID and the scene with synthetic contrast S. By this means, a change in the flow dynamic due to the medical object MO intraoperatively disposed at least partially in the hollow organ may be perceptible in a particularly intuitive manner.

Figure 5:
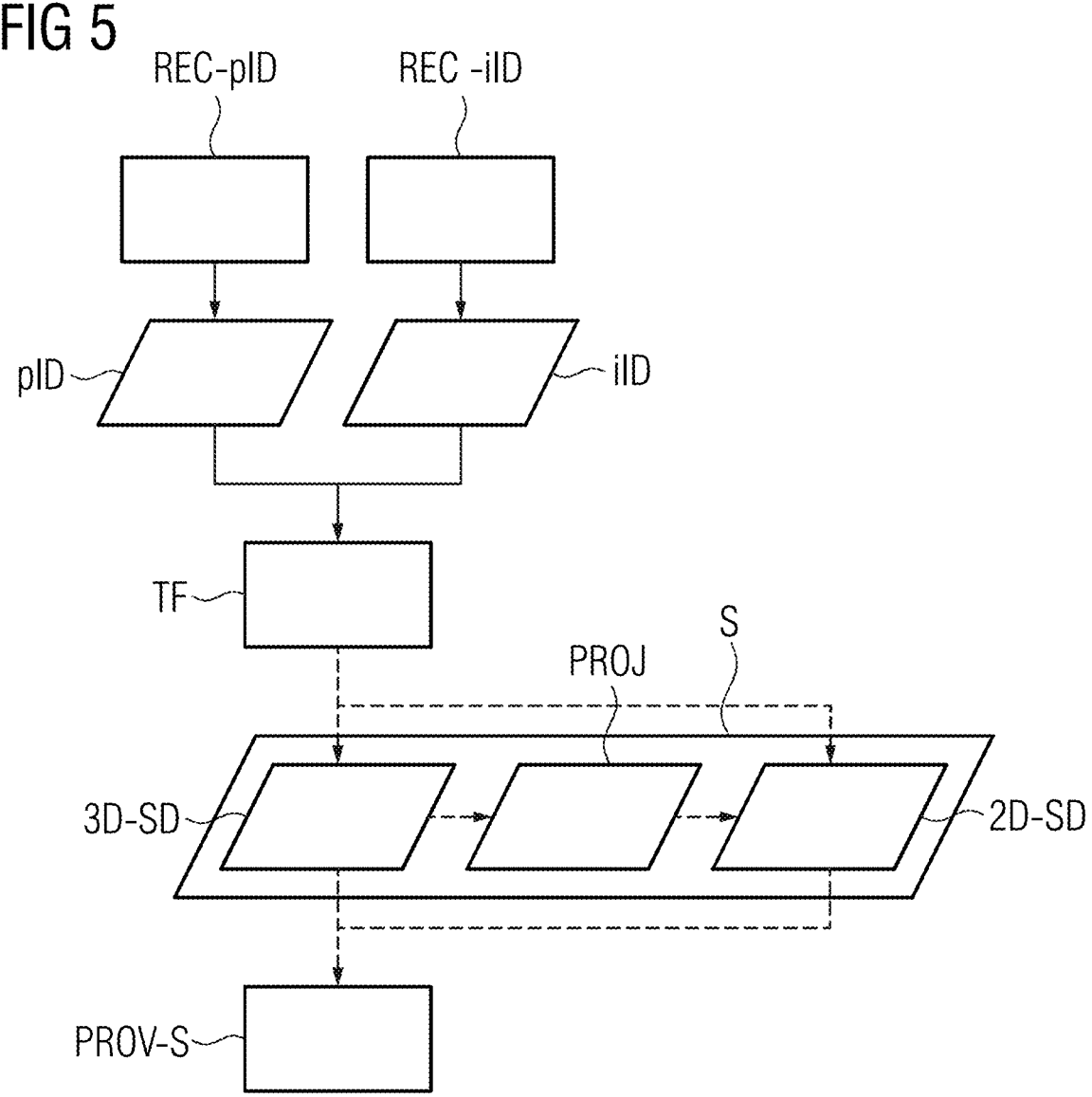
FIG. 5 depicts a schematic representation of a further advantageous embodiment of the proposed method for providing a scene with synthetic contrast.

FIG. 5 depicts a further advantageous embodiment of the proposed computer-implemented method for providing a scene with synthetic contrast PROV-S. In this case, the scene with synthetic contrast S may include a time-resolved 3D image 3D-SD of the virtual contrast agent flow vFI taking into account the medical object at least partially disposed in the hollow organ iHO.

Alternatively, or in addition, the scene with synthetic contrast S may include at least one synthetic time-resolved 2D image 2D-SD of the virtual contrast agent flow vFI taking into account the medical object MO at least partially disposed in the hollow organ iHO. In this case, the at least one synthetic time-resolved 2D image 2D-SD may be generated by a virtual projection PROJ, (e.g., an intensity projection), of the time-resolved 3D image 3D-SD.

Figure 6:
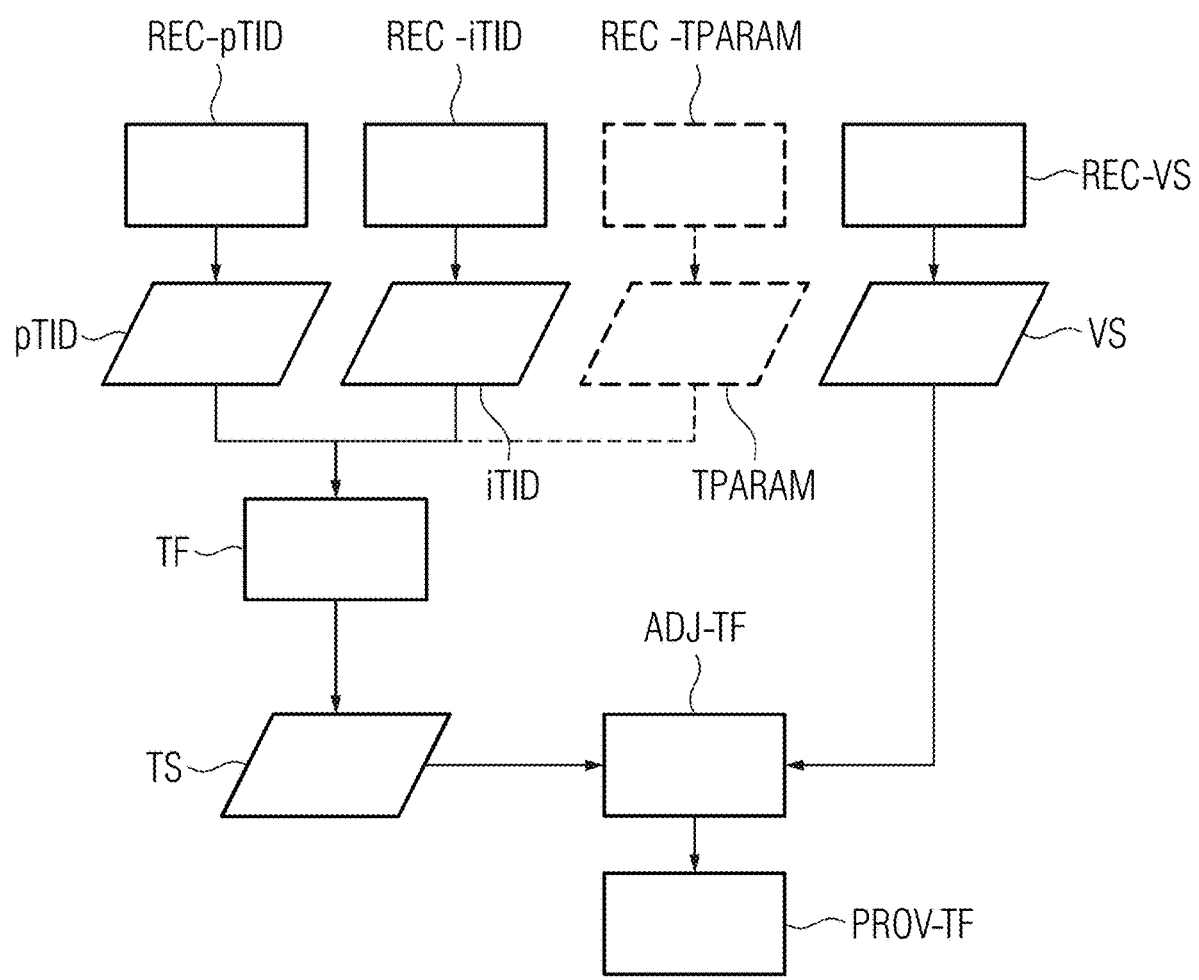
FIGS. 6 to 8 depict schematic representations of different embodiments of the proposed method for providing a trained function.

An advantageous embodiment of a computer-implemented method for providing a trained function PROV-TF is represented schematically in FIG. 6. In this case, in act t.1), preoperative training image data pTID of a training examination region of a training examination subject may be received REC-pTID. The training examination region may contain a hollow organ pHO. Furthermore, the preoperative training image data pTID may image a contrast agent flow pFI in the hollow organ pHO. Intraoperative training image data iTID of the training examination region of the training examination subject may be received REC-iTID in act t.2). In this case, the intraoperative training image data iTID may image a medical object MO at least partially disposed in the hollow organ iHO. A contrast-weighted comparison scene VS of a medical imaging device may be received REC-VS in act t.3). In this case, the contrast-weighted comparison scene VS may image a further contrast agent flow in the hollow organ iHO, (e.g., intraoperatively), the medical object MO being disposed at least partially in the hollow organ. In act t.4), a training scene with synthetic contrast TS may be generated by applying the trained function TF to input data. In this case, the input data may be based on the preoperative image data pTID and the intraoperative training image data iTID. In act t.5), at least one parameter of the trained function TF may be adjusted ADJ-TF based on a comparison between the training scene TS and the comparison scene. The trained function TF may be provided PROV-TF in act t.6).

Furthermore, the proposed method for providing a trained function PROV-TF may include a receiving REC-TPARAM of a training parameter TPARAM, which training parameter TPARAM may include a training material parameter and/or a training operating parameter and/or training shape information relating to the medical object MO and/or a physiological training parameter of the training examination subject. Advantageously, the input data of the trained function TF may be based in addition on the training parameter TPARAM. In this case, the training parameter TPARAM may be provided by the medical object MO, in particular by a processing unit of the medical object MO. Furthermore, the training parameter TPARAM, (e.g., the physiological training parameter of the training examination subject), may be provided by a sensor for detecting the physiological training parameter, (e.g., a breath sensor and/or a motion sensor and/or a pulse sensor and/or a blood pressure sensor).

Furthermore, the training parameter TPARAM may include a training parameter for the contrast agent flow pFI and/or for the virtual contrast agent flow vFI, which training parameter may specify a dose and/or motion speed and/or motion direction of the virtual contrast agent flow vFI.

Figure 7:
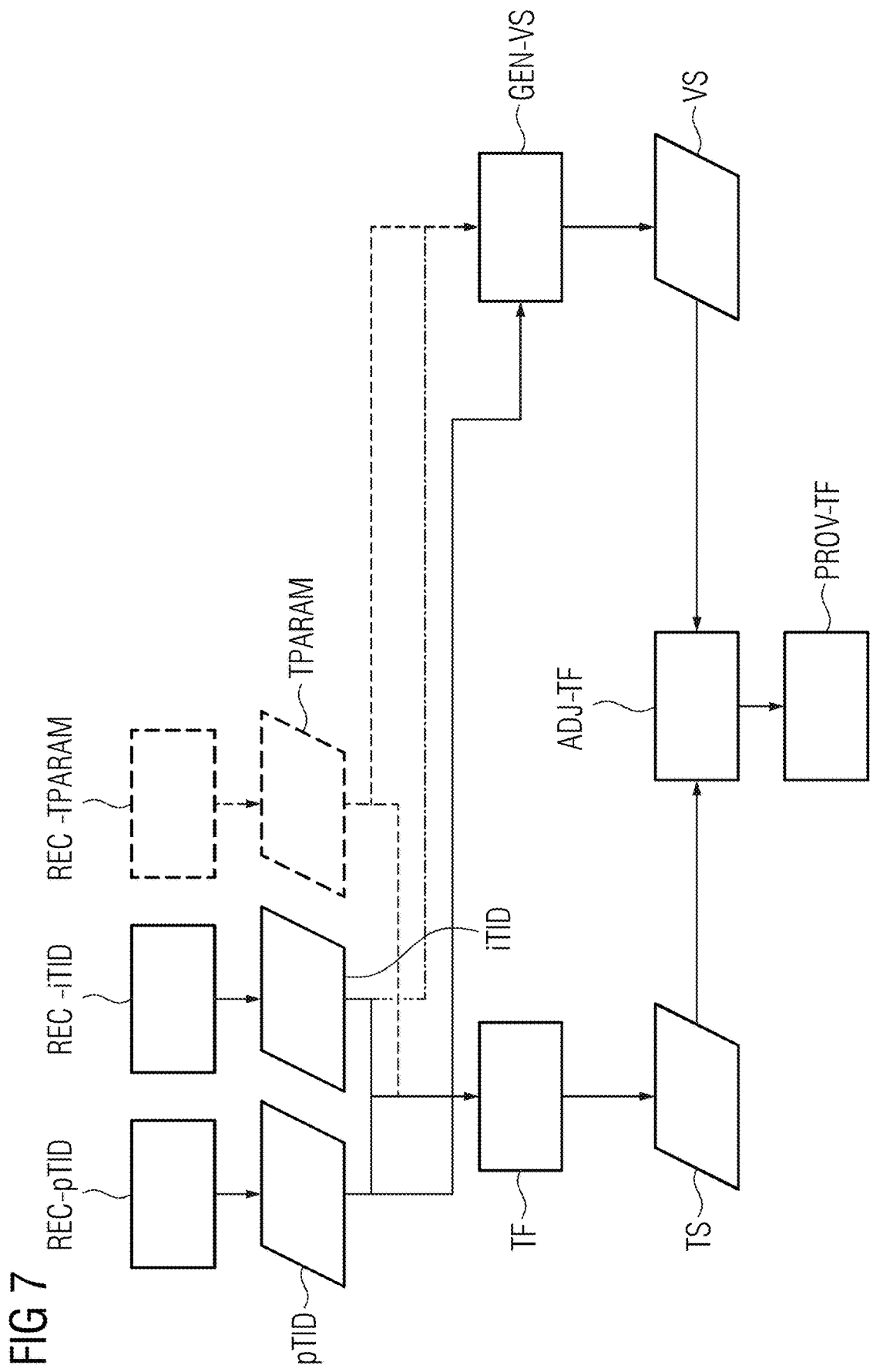

FIG. 7 depicts a further advantageous embodiment of the proposed computer-implemented method for providing a trained function PROV-TF. In this case, in act t.3), in particular alternatively or in addition to the embodiment shown in FIG. 6, a comparison scene with synthetic contrast VS may be generated GEN-VS by applying a deformation correction to the preoperative training image data pTID. In this case, the deformation correction may advantageously be based on the intraoperative training image data iTID, in particular on a spatial progression of the medical object MO imaged in the intraoperative training image data iTID. Furthermore, the comparison scene with synthetic contrast VS may image a virtual comparison contrast agent flow in the hollow organ iHO taking into account the medical object MO at least partially disposed therein. Also, the virtual comparison contrast agent flow may be simulated based on the training parameter TPARAM, in particular the training material parameter and/or the training operating parameter and/or the training shape information relating to the medical object MO.

Advantageously, the virtual comparison contrast agent flow may be simulated in this case taking into account a deformation and/or constriction of the cross-section of the hollow organ iHO due to the medical object MO.

Figure 8:
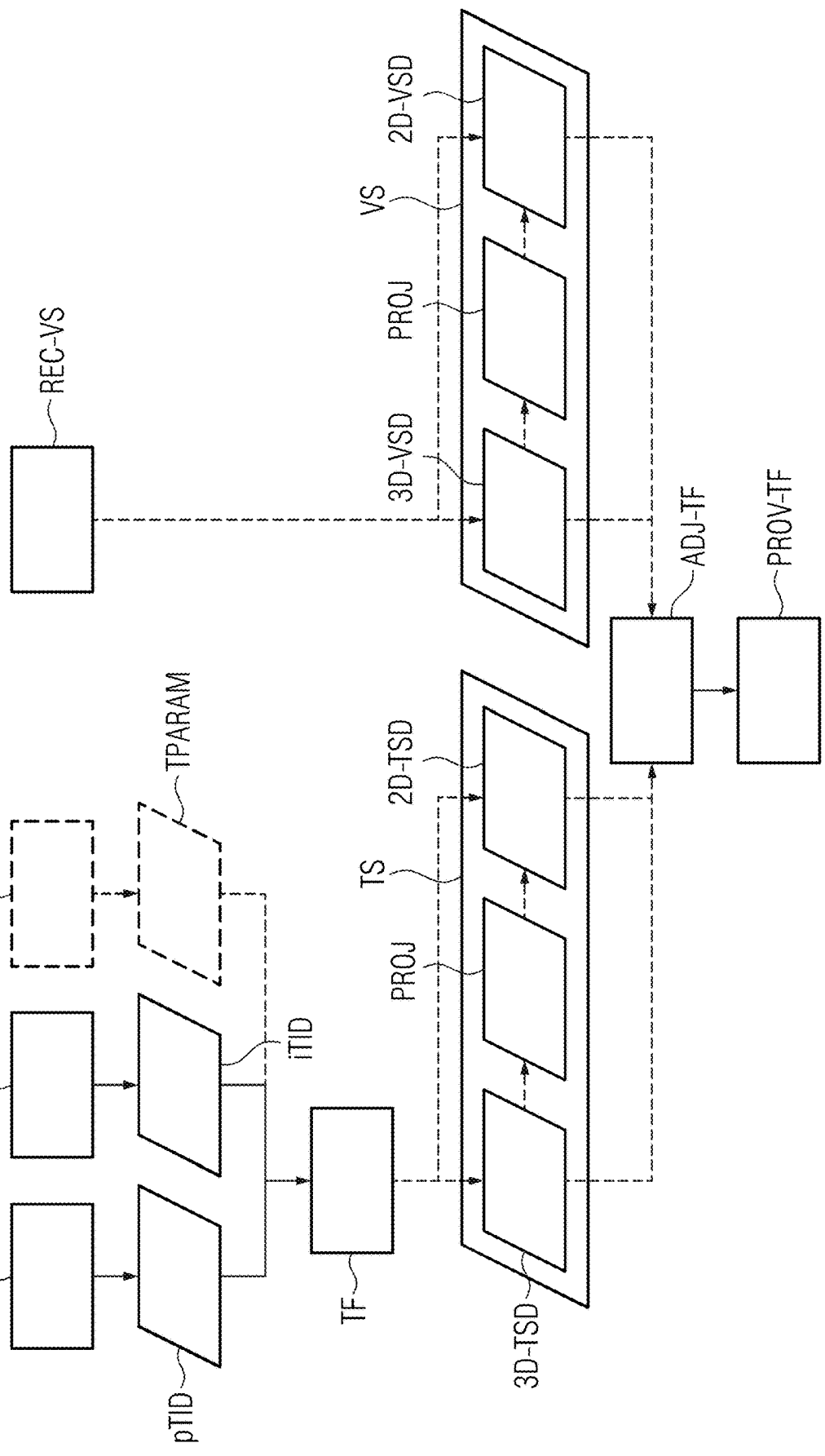

FIG. 8 depicts a further advantageous embodiment of the proposed computer-implemented method for providing a trained function PROV-TF. In this case, the comparison scene VS may include a time-resolved 3D comparison image 3D-VSD of the further contrast agent flow and/or of the virtual comparison contrast agent flow taking into account the medical object MO at least partially disposed in the hollow organ iHO. Alternatively, or in addition, the comparison scene VS may include at least one time-resolved 2D comparison image 2D-VSD of the further contrast agent flow and/or of the virtual comparison contrast agent flow taking into account the medical object MO at least partially disposed in the hollow organ iHO. In particular, the at least one time-resolved 2D comparison image 2D-SD may be generated by a virtual projection PROJ, (e.g., an intensity projection), of the time-resolved 3D comparison image 3D-VSD.

Analogously thereto, the training scene TS may include a time-resolved 3D training image 3D-TSD of the virtual contrast agent flow taking into account the medical object MO at least partially disposed in the hollow organ iHO. Alternatively or in addition, the training scene TS may include at least one time-resolved 2D training image 2D-TSD of the virtual contrast agent flow taking into account the medical object MO at least partially disposed in the hollow organ iHO. The comparison between the training scene TS and the comparison scene VS may advantageously include a comparison between the time-resolved 3D training image 3D-TSD and the time-resolved 3D comparison image 3D-VSD. Alternatively, or in addition, the comparison between the training scene TS and the comparison scene VS may include a comparison between the at least one time-resolved 2D training image 2D-TSD and the at least one time-resolved 2D comparison image 2D-VSD. Advantageously, the at least one parameter of the trained function TF may be adjusted ADJ-TF in such a way that the respective deviation may be minimized.

In particular, the at least one time-resolved 2D training image 2D-TSD may be generated by a virtual projection of the time-resolved 3D training image 3D-TSD. This may be advantageous for the comparison between the training scene and the comparison scene in particular when the comparison scene only contains at least one 2D comparison image 2D-VSD.

Figure 9:
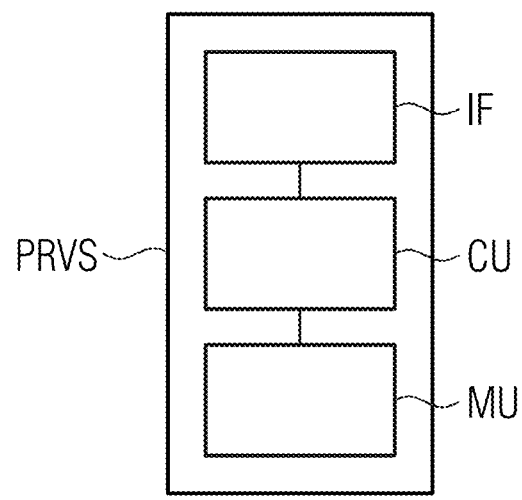
FIG. 9 depicts a schematic representation of an example of a provisioning unit.

A proposed provisioning unit PRVS is schematically represented in FIG. 9. In this case, the provisioning unit PRVS may include an interface IF, a computing unit CU, and a memory unit MU. The provisioning unit PRVS may be embodied to perform a method for providing a scene with synthetic contrast and its aspects in that the interface IF, the computing unit CU, and the memory unit MU are embodied to perform the corresponding method acts. In particular, the interface IF may be embodied for performing acts b.1), b.2) and/or b.4). Furthermore, the computing unit CU and/or the memory unit MU may be embodied for performing act b.3).

Figure 10:
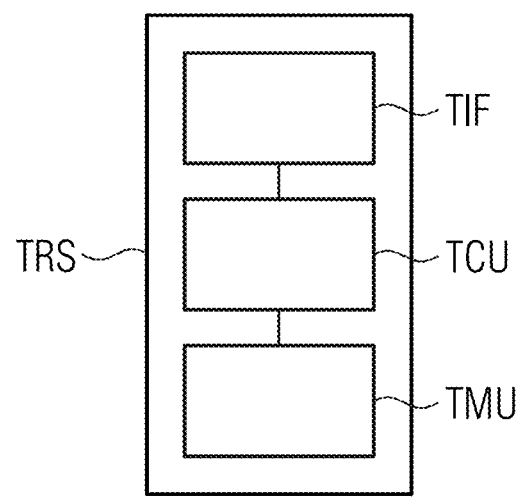
FIG. 10 depicts a schematic representation of an example of a training unit.

FIG. 10 depicts a schematic representation of a proposed training unit TRS. The training unit TRS may advantageously include a training interface TIF, a training memory unit TMU, and a training computing unit TCU. The training unit TRS may be embodied to perform a method for providing a trained function PROV-TF and its aspects in that the training interface TIF, the training memory unit TMU, and the training computing unit TCU are embodied to perform the corresponding method acts. In particular, the training interface TIF may be embodied to perform acts t.1), t.2), t.3), and/or t.6). Furthermore, the training computing unit TCU and/or the training memory unit TMU may be embodied to perform acts t.3) to t.5).

The provisioning unit PRVS and/or the training unit TRS may be a computer, a microcontroller, or an integrated circuit. Alternatively, the provisioning unit PRVS and/or the training unit TRS may be a real or virtual network of interconnected computers (a technical term for a real network is "cluster"; a technical term for a virtual network is "cloud"). The provisioning unit PRVS and/or the training unit TRS may also be embodied as a virtual system that is implemented on a real computer or a real or virtual network of interconnected computers (virtualization).

An interface IF and/or a training interface TIF may be a hardware or software interface (for example, PCI bus, USB, or Firewire). A computing unit CU and/or a training computing unit TCU may include hardware elements or software elements, (e.g., a microprocessor or a Field Programmable Gate Array (FPGA)). A memory unit MU and/or a training memory unit TMU may be realized as a volatile working memory known as Random Access Memory (RAM) or as a nonvolatile mass storage device (e.g., hard disk, USB stick, SD card, or Solid State Disk (SSD)).

The interface IF and/or the training interface TIF may include a number of subsidiary interfaces that perform different acts of the respective methods. In other words, the interface IF and/or the training interface TIF may also be understood as a plurality of interfaces IF or a plurality of training interfaces TIF. The computing unit CU and/or the training computing unit TCU may include a number of subsidiary computing units that perform different acts of the respective methods. In other words, the computing unit CU and/or the training computing unit TCU may also be understood as a plurality of computing units CU or a plurality of training computing units TCU.

Figure 11:
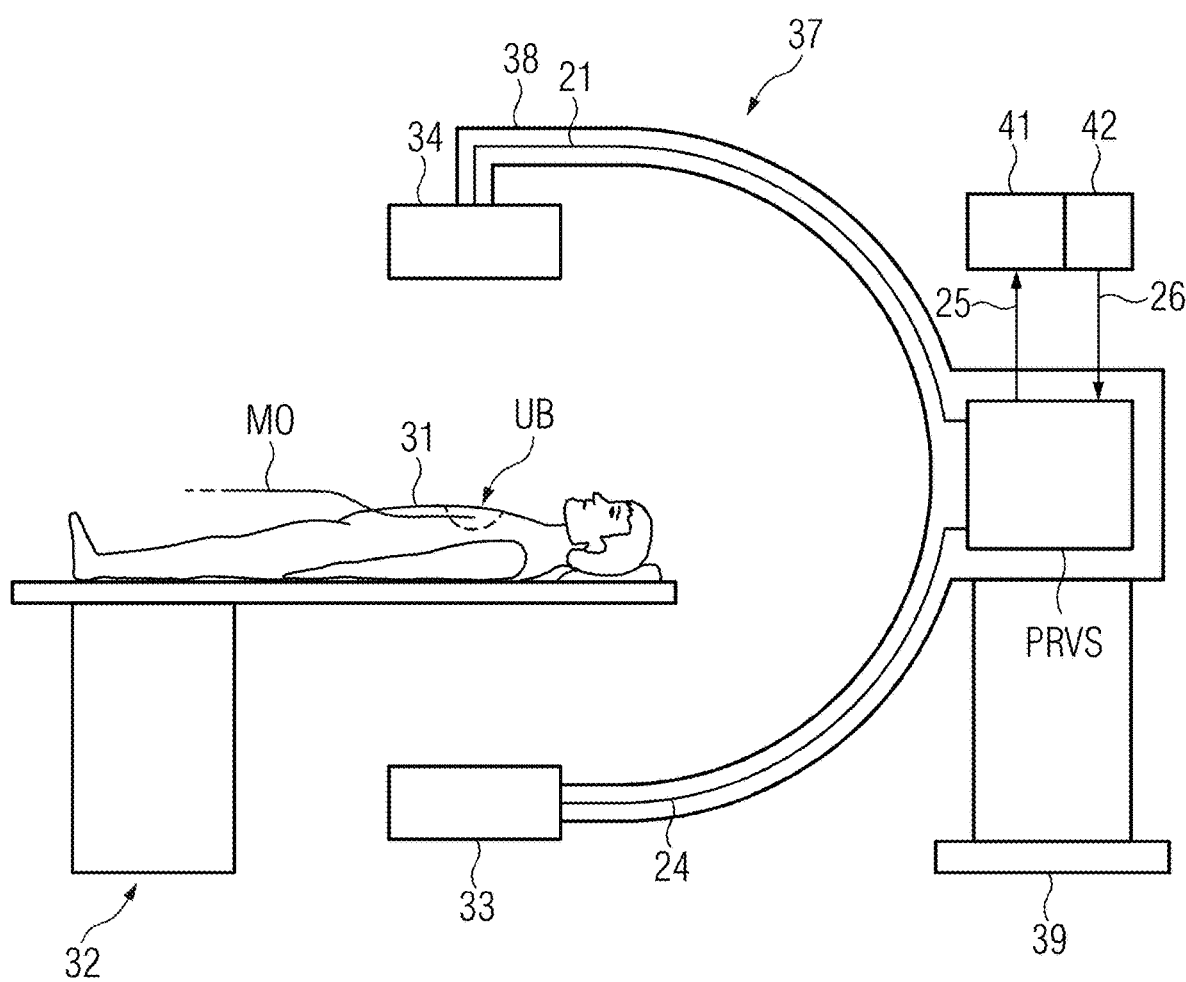
FIG. 11 depicts a schematic representation of a medical C-arm x-ray device as an exemplary embodiment of a proposed medical imaging device.

In FIG. 11, a medical C-arm x-ray device 37 is illustrated schematically as an example of a proposed medical imaging device. In this case, the medical C-arm x-ray device 37 may advantageously include a provisioning unit PRVS. Furthermore, the medical C-arm x-ray device 37, (e.g., the provisioning unit PRVS), may be embodied to perform a proposed method for providing a scene with synthetic contrast PROV-S.

In this case, the medical C-arm x-ray device 37 advantageously includes a detector 34, (e.g., an x-ray detector), and an x-ray source 33. In order to acquire the preoperative image data pID and the intraoperative image data iID, an arm 38 of the C-arm x-ray device 37 may be mounted so as to be movable about one or more axes. The medical C-arm x-ray device 37 may further include a motion device 39 which enables the C-arm x-ray device 37 to execute a movement in space.

For the purpose of acquiring the preoperative image data pID and the intraoperative image data iID of an examination region UB of an examination subject 31 disposed on a patient support and positioning device 32, the provisioning unit PRVS may send a signal 24 to the x-ray source 33. The x-ray source 33 may thereupon transmit a pencil beam of x-rays. When the pencil beam of x-rays, following an interaction with the examination region UB, is incident on a surface of the detector 34, the detector 34 may send a signal 21 to the provisioning unit PRVS. The provisioning unit PRVS may receive the preoperative image data pID and/or the intraoperative image data iID, for example, on the basis of the signal 21.

Furthermore, the medical C-arm x-ray device 37 may include an input unit 42, (e.g., a keyboard), and/or a visualization unit 41, (e.g., a monitor and/or display). The input unit 42 may be integrated into the visualization unit 41, (e.g., in the case of a capacitive input display). In this case, the medical C-arm x-ray device 37, (e.g., the proposed method for providing a scene with synthetic contrast PROV-S), may be controlled by an input by a user at the input unit 42. The input unit 42 may also allow an input by the user in order to specify a value for the parameter PARAM. For this purpose, the input unit 42 may send a signal 26 to the provisioning unit PRVS.

Furthermore, the visualization unit 41 may be embodied to display information and/or graphical representations of information of the medical C-arm x-ray device 37 and/or of the provisioning unit PRVS and/or of further components. For this purpose, the provisioning unit PRVS may send a signal 25 to the visualization unit 41. In particular, the visualization unit 41 may be embodied to display a graphical representation of the preoperative image data pID and/or the intraoperative image data pID and/or the scene with synthetic contrast S.

The schematic representations contained in the described figures do not reflect a scale or proportions of any kind.

In conclusion, it is pointed out once again that the methods described in detail in the foregoing, as well as the illustrated devices, are simply exemplary embodiments which may be modified in the most diverse ways by the person skilled in the art without leaving the scope of the disclosure. Furthermore, the use of the indefinite articles "a" or "an" does not exclude the possibility that the features in question may also be present more than once. Similarly, the terms "unit" and "element" do not rule out the possibility that the components in question includes a plurality of cooperating subcomponents, which, if necessary, may also be distributed in space.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for providing a scene with synthetic contrast, the method comprising:
receiving preoperative image data of an examination region of an examination subject, wherein the examination region comprises a hollow organ, and wherein the preoperative image data images a contrast agent flow in the hollow organ;
receiving intraoperative image data of the examination region of the examination subject, wherein the intraoperative image data images a medical object at least partially disposed in the hollow organ;
generating the scene with the synthetic contrast by applying a trained function to input data, wherein the input data is based on the preoperative image data and the intraoperative image data, wherein the scene with the synthetic contrast comprises an image of a virtual contrast agent flow in the hollow organ taking into account the medical object at least partially disposed therein, wherein the virtual contrast agent flow comprises a predefined contrast value and/or intensity curve with respect to anatomical structures and/or tissue of the examination subject, and wherein at least one parameter of the trained function is based on a comparison between a training scene and a comparison scene; and providing the scene with the synthetic contrast, wherein the training scene has been generated with the synthetic contrast by applying the trained function to training input data, wherein the training input data is based on preoperative training image data and intraoperative training image data, and wherein the comparison scene with the synthetic contrast has been generated by applying a deformation correction to the preoperative training image data, wherein the deformation correction is based on the intraoperative training image data.

2. The method of claim 1, wherein the scene with the synthetic contrast comprises a time-resolved three-dimensional (3D) image of the virtual contrast agent flow taking into account the medical object at least partially disposed in the hollow organ.

3. The method of claim 2, wherein the scene with the synthetic contrast comprises at least one synthetic time-resolved two-dimensional (2D) image of the virtual contrast agent flow taking into account the medical object at least partially disposed in the hollow organ.

4. The method of claim 3, wherein the at least one synthetic time-resolved 2D image is generated by a virtual projection of the time-resolved 3D image.

5. The method of claim 1, wherein the scene with the synthetic contrast comprises at least one synthetic time-resolved two-dimensional (2D) image of the virtual contrast agent flow taking into account the medical object at least partially disposed in the hollow organ.

6. The method of claim 1, wherein the input data is additionally based on a material parameter relating to the medical object, an operating parameter relating to the medical object, shape information relating to the medical object, a physiological parameter of the examination subject, or a combination thereof.

7. The method of claim 1, wherein the input data is additionally based on a parameter for the virtual contrast agent flow, and wherein the parameter specifies one or more of a dose, a motion speed, or a motion direction of the virtual contrast agent flow.

8. A provisioning unit comprising:

an interface;

a microprocessor; and a memory, wherein the interface, the memory, and the microprocessor are configured to:

receive preoperative image data of an examination region of an examination subject, wherein the examination region comprises a hollow organ, and wherein the preoperative image data images a contrast agent flow in the hollow organ;

receive intraoperative image data of the examination region of the examination subject, wherein the intraoperative image data images a medical object at least partially disposed in the hollow organ;

generate a scene with a synthetic contrast by applying a trained function to input data, wherein the input data is based on the preoperative image data and the intraoperative image data, wherein the scene with the synthetic contrast comprises an image of a virtual contrast agent flow in the hollow organ taking into account the medical object at least partially disposed therein, wherein the virtual contrast agent flow comprises a predefined contrast value and/or intensity curve with respect to anatomical structures and/or tissue of the examination subject, and wherein at least one parameter of the trained function is based on a comparison between a training scene and a comparison scene; and provide the scene with the synthetic contrast, wherein the training scene has been generated with synthetic contrast by applying the trained function to training input data, wherein the training input data is based on preoperative training image data and intraoperative training image data, and wherein the comparison scene with the synthetic contrast has been generated by applying a deformation correction to the preoperative training image data, wherein the deformation correction is based on the intraoperative training image data.

9. The provisioning unit of claim 8, wherein the provisioning unit is a component of a medical imaging device.

10. A computer-implemented method for providing a scene with synthetic contrast, the method comprising:

receiving preoperative image data of an examination region of an examination subject, wherein the examination region comprises a hollow organ, and wherein the preoperative image data images a contrast agent flow in the hollow organ;

receiving intraoperative image data of the examination region of the examination subject, wherein the intraoperative image data images a medical object at least partially disposed in the hollow organ;

generating the scene with the synthetic contrast by applying a trained function to input data, wherein the input data is based on the preoperative image data and the intraoperative image data, wherein the scene with the synthetic contrast comprises an image of a virtual contrast agent flow in the hollow organ taking into account the medical object at least partially disposed therein, and wherein at least one parameter of the trained function is based on a comparison between a training scene and a comparison scene; and providing the scene with the synthetic contrast, wherein the trained function is derived by:

receiving preoperative training image data of a training examination region of a training examination subject, wherein the training examination region comprises a further hollow organ, and wherein the preoperative training image data images a further contrast agent flow in the further hollow organ;

receiving intraoperative training image data of the training examination region of the training examination subject, wherein the intraoperative training image data images a further medical object at least partially disposed in the further hollow organ;

receiving a contrast-weighted comparison scene of a medical imaging device, wherein the contrast-weighted comparison scene images the further contrast agent flow in the further hollow organ, wherein the further medical object is at least partially disposed in the further hollow organ, and/or generating a further comparison scene with the synthetic contrast by applying a deformation correction to the preoperative training image data, wherein the deformation correction is based on the intraoperative training image data, wherein the comparison scene with the synthetic contrast comprises a further image of a virtual comparison contrast agent flow in the further hollow organ taking into account the further medical object at least partially disposed therein, and wherein the virtual comparison contrast agent flow is simulated;

generating the training scene with the synthetic contrast by applying the trained function to training input data, wherein the training input data is based on the preoperative training image data and the intraoperative training image data; and adjusting the at least one parameter of the trained function based on the comparison between the training scene and the comparison scene.

* * * * *